United States Patent [19]

Takada

[11] Patent Number: 5,350,741
[45] Date of Patent: Sep. 27, 1994

[54] ENTERIC FORMULATIONS OF PHYSIOLOGICALLY ACTIVE PEPTIDES AND PROTEINS

[76] Inventor: Kanji Takada, 618-2 Gokomachidori Gojoagaru Azuchi-chou, Shimogyo-ku, Kyoto-shi, Kyoto 600, Japan

[21] Appl. No.: 888,324

[22] Filed: May 26, 1992

Related U.S. Application Data

[63] Continuation of Ser. No. 474,089, Mar. 30, 1990, abandoned.

[30] Foreign Application Priority Data

Jul. 30, 1988 [JP] Japan ................. 63-191185

[51] Int. Cl.⁵ .............................. A61K 37/02
[52] U.S. Cl. ........................ 514/3; 424/85.1; 424/464; 424/472; 424/477; 424/484; 424/501; 424/502; 514/2; 514/11; 514/12; 514/19
[58] Field of Search ............ 514/2, 3, 11, 12, 19; 424/85.1, 501, 502, 464, 472, 477, 484

[56] References Cited

U.S. PATENT DOCUMENTS

| | | |
|---|---|---|
| 3,909,444 | 9/1975 | Anderson et al. |
| 3,960,757 | 6/1976 | Morishita et al. |
| 4,415,547 | 11/1983 | Yu et al. |
| 4,562,061 | 12/1985 | Appelgren et al. |
| 4,684,516 | 8/1987 | Bhutani ................. 424/19 |
| 4,716,041 | 12/1987 | Kjornaes et al. |
| 4,758,437 | 7/1988 | Takashi et al. .......... 424/471 |
| 4,968,506 | 11/1990 | Appelgren et al. |

FOREIGN PATENT DOCUMENTS

| | | |
|---|---|---|
| 0063014 | 10/1982 | European Pat. Off. |
| 0225189 | 6/1987 | European Pat. Off. |
| 59-20219 | 2/1984 | Japan . |
| 2057876 | 4/1981 | United Kingdom . |
| 2066070 | 7/1981 | United Kingdom . |

OTHER PUBLICATIONS

Takada et al., Chemical Abstracts, vol. 107, No. 6, Abstract No. 46298j, (Aug. 1987).
CA, vol. 110, #20, Abstract, #179441j, (May 15, 1989), K. Takada et al.
Abstract of JA 5920219 (Feb. 1984).
Takada et al., CA 107: No. 6 (Dec. 1986).
O'Hagen et al., "Intestinal Absorption of Proteins, etc.", *CRC Critical Reviews in Therapeutic Drug Carrier Systems*, vol. 4, Issue 3, (1987), pp. 197–221.
Takada et al., "Enteric Solid Dispersion, etc.", *Chem. Pharm. Bull.*, 37(2), 471–474 (Feb. 1989).

*Primary Examiner*—Lester L. Lee
*Attorney, Agent, or Firm*—Millen, White, Zelano & Branigan

[57] ABSTRACT

An enteric formulation for a proteinous drug which protects it from enzymatic degradation and promotes its uptake by the intestinal tract when administered orally, comprises either a solid mass of an intimate mixture of the drug, a nontoxic nonionic surfactant, and an enteric material, or a solid mass of an intimate mixture of the drug with the nonionic surfactant covered by a discrete enteric coating.

20 Claims, 6 Drawing Sheets

ENTERIC FORMULATIONS OF PHYSIOLOGICALLY ACTIVE PEPTIDES AND PROTEINS

This application is a continuation of application Ser. No. 07/474,089, filed Mar. 30, 1990, now abandoned, based on PCT/JP89/00748 filed Jul. 26, 1989.

BACKGROUND OF THE INVENTION

This invention relates to a pharmaceutical formulation containing a physiologically active peptides or protein as an active principle.

A number of physiologically active peptides and proteins are currently used for therapeutic purposes. Enzymatic degradation and poor absorption of these substances from the intestinal tract have historically limited their administration to the parenteral route. The blood level of a drug is a function of the rate of its uptake by the living body (bioavailability) and the rate of its removal from the body (clearance). In the case of the oral administration of peptides or proteins, poor absorption from the intestinal tract is the main factor that precludes the dose-dependent delivery of the drug into the blood stream by this route.

Attempts have been made to increase the intestinal absorption of proteinous drugs by the use of formulations that protect the drugs from enzymatic degradation and/or enhance the uptake into the intestinal mucosa. These include a combination of insulin and a chymotrypsin-inhibitor (J. Pharm. Pharmcol., 37 (1985), 545–549); coating with azoaromatic copolymers (Science, 233 (1986), 1081–1084); a combination of vasopressin and aprotinin as a proteolytic enzyme inhibitor (J. Pharm. Sci., 77 (1988), 33–38); a solid solution of insulin in a mixture of stearic acid and a surfactant sold under the trademark "Brij" (J. Pharm. Pharmcol., 33 (1981), 733–734); and the like. However, none of these approaches have been proven satisfactory. They are not suited for application to proteinous drugs in general. Some of these techniques require the use of co-ingredients which have not been established to be pharmaceutically acceptable. Others often exhibit undesirable side effects such as vomiting.

By the present invention, there is provided an enteric formulation of physiologically active proteins or peptides (hereinafter referred to as "proteinous drug") in which the active principle is easily absorbed from the intestinal Tract and delivered into the blood stream in a substantially dose-dependent manner. The present invention utilizes such co-ingredients that have been proven to be pharmaceutically acceptable or inert and, therefore, are those commonly used for the manufacture of various forms of solid medicaments for oral administration. Accordingly, the formulation of the invention is substantially free from any side effect or otherwise adverse action due to the presence of such co-ingredients. One of the significant advantages of this invention resides in the fact that its application is not limited to a particular class of proteinous drugs but finds use in proteinous products in general.

Many proteinous drugs occur as a solution which must be stored in a cool place, or a lyophilized product which requires subsequent reconstitution in saline or sterile water immediately before use. By the present invention, such drugs may be formulated in a solid medicament for oral administration which is stable for a reasonable period of time and may be administered directly to the patient without the need for reconstitution or other processing. This also achieves transportation and storage advantages over current preparations.

Other objects and advantages of the present invention will become apparent to those skilled in the art as the description proceeds.

SUMMARY OF THE INVENTION

According to the present invention, an enteric, pharmaceutical formulation having an enhanced bioavailability is provided comprising a solid mass of an intimate mixture of a proteinous drug, a nontoxic, nonionic surfactant, and a pharmaceutically acceptable, enteric material capable of dissolving in duodenal juice and also in volatile organic solvent.

DETAILED DISCUSSION

The enteric material is a polymeric material used for forming enteric coating on tablets and like. When the active principle is a peptide or protein which is susceptible to enzymatic degradation in the intestinal tract, an organic acid such as tartaric acid and/or an inhibitor of proteolytic enzymes may be used in combination with the nonionic surfactant so as to suppress the action of the proteolytic enzyme. In this case, a less than equivalent amount to the organic acid of a carbonate salt such as sodium bicarbonate may be incorporated to give an effervescent formulation.

Preferably, at least 50%, more preferably not less than 80% by weight of the entire composition is occupied by the enteric material acting as a carrier. The amount of surfactant may vary with the amount of the active principle present in the formulation but must be sufficient to promote the uptake of active principle into the intestinal mucosa while protecting the same from enzymatic degradation in the form of micelles.

The formulation of this invention may be prepared using any conventional technique, for example, by dissolving the surfactant and the enteric material in an organic solvent, intimately dispersing the active principle in the solution, evaporating the mixture preferably under vacuum to dryness and pulverizing the resulting mass.

The resulting powder may be administered as such or shaped into granules or other particulate forms. The particulate formulation may be further processed if desired, into tablets, capsules or other unit dosage forms for oral administration.

Alternatively, the enteric material may be present as a discrete coating covering a solid mass of an intimate mixture of other ingredients. Thus, the present invent ion provides an enteric formulation comprising a solid mass of an intimate mixture of the proteinous drug and a nontoxic, nonionic surfactant, and a coating of the enteric material covering the solid mass. When the particulate formulation having a discrete enteric coating is desired, the above procedure may be followed up to the shaping step, without initially admixing the enteric material, but instead forming an enteric coating on the shaped particles using any conventional technique.

A number of physiologically active peptides and proteins are known and find various therapeutic uses. They may be naturally occurring or recombinant products. Physiologically active peptides include not only intact peptides but also their fragments, their family in which one or more constituent amino acids are defective or have been replaced by other amino acids. The term "protein" as used herein also includes glycoproteins.

Non-limiting examples thereof include angiotensin II antagonist peptide, bradykinin, calcitonin-gene associated factor, tissue plasminogen activators, cholecystokinin, delta sleep-inducing peptide (DSIP), β-endorphin, atriopeptin, α-and β-melanocyte-stimulating hormone, nerve peptide, nerve growth factor (NGF), gastrin antagonist peptide, neurotensin, somatostatin, colony-stimulating factors such as G-CSF and GM-CSF, interferon, thymopoietin, tumor necrosis factor, growth hormone, growth hormone-carrier protein complex, human atrial natriuretic peptide (HANP), insulin, luteinizing hormone-releasing factor (LHRH), streptokinase, erythropoietin, urokinase, lysozyme, vasopressin (8-lysine and 8-arginine), oxytocin, desmopressin, cytochome C, histamin-releasing factor, platelet related growth factor, human chorionic gonadotropin (HCG), human growth hormone (HGH), adrenocorticotropin (ACTH), calcitonin, parathyroid hormone, Factor XIII, Factor IX, MSH release inhibiting factor, enkephalin, thyrotropin releasing hormone, interleukins such as interleukin-3, renin inhibitor peptides, and the like.

In one important aspect of this invention, the proteinous drug may be cyclosporines, i.e., cyclosporin A, cyclosporin B, cyclosporin C, cyclosporin D and cyclosporin G, which are known to be cyclic oligopeptides having immunosuppressive activity. The term "cyclosporines" as used herein also include those in which one or more amino acids constituting the natural cyclosporines are chemically modified, substituted by other amino acids or removed. Cyclosporines are hardly soluble in water and, therefore oily solutions such as in olive oil have been used for therapeutic application.

A solid, enteric formulation of cyclosporines may be prepared by the present invention which has storage, transportation and administration advantages over the oily preparation.

Surfactants are incorporated into the formulation of this invention to serve as an agent for promoting the absorption of protenous drugs by the intestinal tract and also for forming the drug into micelles which protect the same from enzymatic degradation. Any nonionic surfactant soluble in a conventional organic solvent such as methanol, ethanol, acetone, ethoxyethanol, methylene chloride and mixtures of these solvents may be used to advantage. Examples thereof include sorbitan fatty acid ester, polyoxyethylenesorbitan fatty acid ester, polyoxyethylene-hydrogenated castor oil, fatty acid alkanolamide, sucrose fatty acid esters, glycerol mono-, di- and trioctanoate. A minor proportion of anionic surfactants such as capric acid or bile salts may be tolerated.

The preparation of this invention contains at least 50%, preferably not less than 80% by weight based on the entire composition of an enteric material capable of dissolving in a conventional organic solvent as previously mentioned and also in the duodenal juice. They must be, of course, nontoxic and pharmaceutically acceptable or otherwise have no adverse effect on the active principle. Typically the enteric material is selected from semisynthetic or synthetic polymers having free carboxyl function that have been commonly used for forming an enteric coating on tablets and other orally administered solid medicaments. Examples thereof include cellulose acetate phthalate, hydroxypropylmethylcellulose succinate, hydroxypropylmethylcellulose phthalate, carboxylmethylethylcellulose, methacrylic acid-methyl methacrylate copolymer, and the like. Optionally incorporated are conventional pharmaceutical excipients such as sugars, e.g., glucose, maltose or sorbitol; organic acids, e.g., tartaric, malonic, maleic, malic, citric or cinnamic; neutral solid materials, e.g., urea; and hydrophilic polymers, e.g., polyethylene glycol, polyvinylpyrrolidone, cyclodextrin, and polyvinyl alcohol. Mixtures of the above-mentioned excipients may be used. For example, the formulations may comprise an organic acid of the above-mentioned class to inhibit the action of proteolytic enzymes with or without combining less than an equivalent amount to the acid of a carbonate salt such as sodium bicarbonate.

The above individual ingredients forming the formulation of this invention are intimately mixed together. By the term "intimately", is meant that the ingredients are not individually identifiable by visual inspection of the mixture, as in the case of a solid solution. Alternatively, the enteric material may be present, as previously discussed, not in the mixture but as a discrete coating on the core of a mixture of other ingredients.

The formulation of this invention may be prepared for example, by dissolving the surfactant and the enteric material in an organic solvent, intimately dispersing the active substance in the solution, evaporating the mixture to dryness, and pulverizing the resulting mass. The above dissolving step may be promoted by stirring. The evaporating step is preferably carried out under vacuum. Although the formulation of this invention may assume a powdered form and administered as such, it may also be shaped into granules or other particulate forms, as desired. For example, the powdered formulation may be kneaded with a small amount inert liquid such as water, methanol, ethanol, acetone and the like, extruding the resulting mass through a mesh screen, and drying the extrudate. Effervescent granules may be prepared by incorporating conventional effervescent agents such as sodium bicarbonate. The granules are provided with an enteric coating thereon using the semi-synthetic or synthetic polymers as previously listed when the nature of the carrier material into which the active substance is intimately dispersed is not enteric.

The pharmaceutical preparation of this invention may, of course, comprise other conventional additives such as inhibitors of proteolytic enzymes, coloring agents, flavors, stabilizing agents and the like. Granular or other particulate preparations of this invention may be further processed into desired unit dosage forms such as tablets, capsules and the like.

The following examples are offered for illustrative purposes only. All parts and percents therein are by weight unless otherwise indicated.

EXAMPLE 1

400 mg of L-tartaric acid and 40 mg of polyethylene glycol-hydrogenated castor oil (HCO-60) were dissolved in 5 ml of methanol. This solution was placed in a mortar previously warmed to 30° C. To the solution was added 1.5 mg of recombinant human granulocyte colony-stimulating factor (G-CSF, produced by the method disclosed in PCT Publication WO 87/01132). Immediately after the addition of G-CSF, the mixture was stirred with a pestle under a hot air current (40° C.) and then placed in a desiccator under vacuum overnight to remove the solvent. The resulting solid-mass was pulverized with the pestle and kneaded with 30 mg of sodium bicarbonate and a small amount of 70% ethanol. The mixture was then divided and shaped into pills of about 2 mm size and thoroughly dried. The dried pills were given a coating of hydroxypropylmethylcellulose phthalate (HP-55) to obtain an enteric formulation.

The above procedure was repeated without incorporating sodium bicarbonate therein to obtain a similar formulation.

EXAMPLE 2

A solution of 900 mg of HP-55 and 200 mg of HCO-60 in 2 ml of a 3:10 mixture of methanol and methylene chloride was poured into a vial containing 1.5 mg of lyophilized G-CSF and stirred until the mixture became a solution. This solution was cast into a Teflon tubing segment having a diameter of 3 mm and allowed to stand at room temperature for five hours. Then the tubing segment was placed in a desiccator under vacuum to remove the solvent completely. The resulting solid mass was withdrawn from the Teflon mold and cut into segments of about 2 mm length.

EXAMPLE 3

25 mg of insulin, 400 mg of L-tartaric acid and 40 mg of HCO-60 were dissolved in 5 ml of a 8:2 mixture of methanol and 0.1N HC1. This solution was placed in a mortar previously warmed to 30° C., stirred with a pestle under hot air current (40° C.), then evaporated in a desiccator under vacuum overnight to remove the solvent and pulverized with the pestle. The resulting powder was shaped into granular form with a small amount of 80% ethanol as in Example 1 and processed with HP-55 to give an enteric formulation.

EXAMPLE 4

Figure 5:
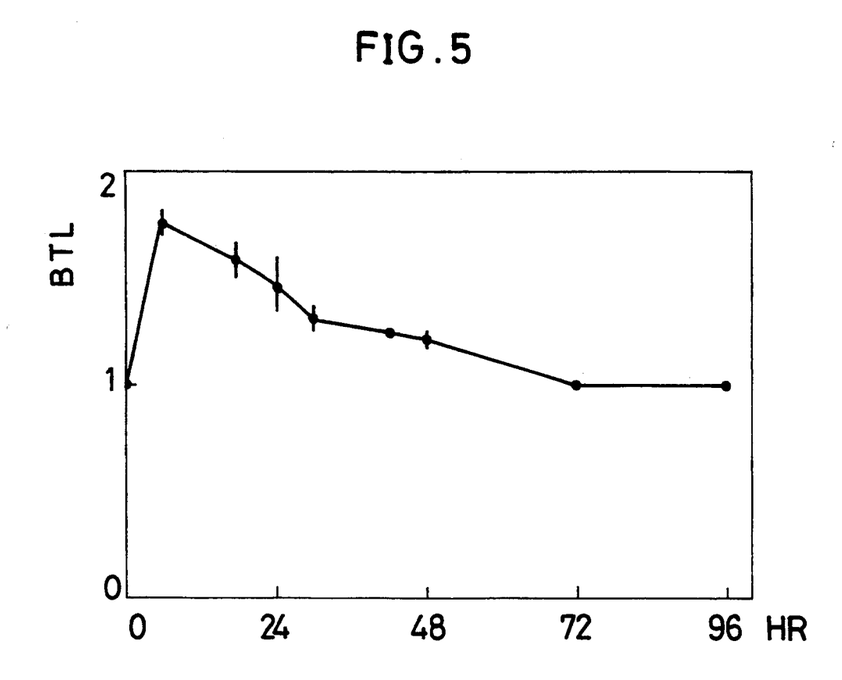
FIG. 5 shows similar dynamics of the group given the non-effervescent preparation of Example 1 at a G-CSF does level of 1.5 Mg/Kg.
Figure 6:
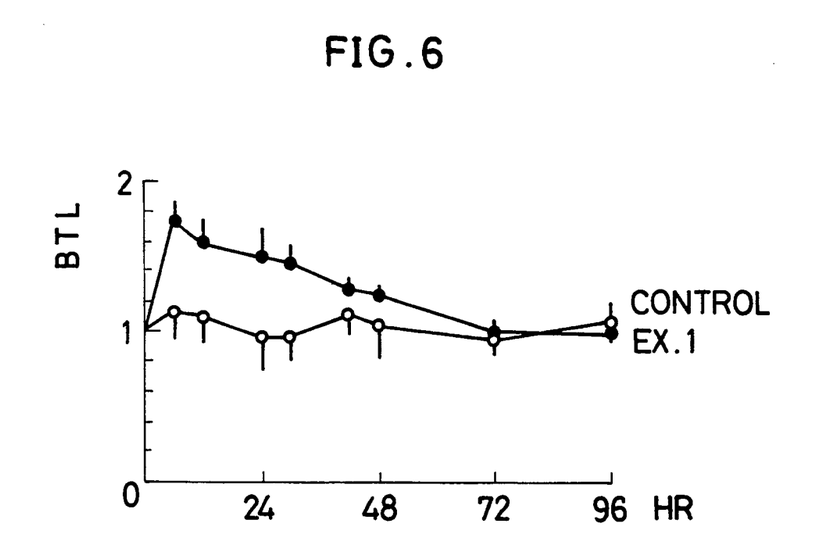
FIG. 6 is a BTL dynamic curve similar to FIG. 2 curve.

Three male Wistar rats, weighing 300–400 g were used in each experiment. The rats were given a dose of the enteric preparation of Example 1 corresponding to 1.5, 0.75 and 0.375 mg/kg of G-CSF, respectively, by administering through an incision on the stomach into the duodenum. The control group was given a placebo preparation which was free of G-CSF but otherwise identical to the preparation of Example 1. Blood samples were taken from the tail artery before the administration of the test preparations and subsequent to the administration over 4 days. The blood total leucocyte (BTL) counts were determined and expressed as the relative value, which was obtained by dividing the BTL count by the respective control BTL count. The results obtained are shown in the accompanying drawings, in which FIGS. 1, 2, 3 and 4 illustrate BTL dynamics obtained by the administration of the effervescent preparation of Example 1 at a G-CSF dose level of zero (control), 1.5 mg/kg, 0.75 mg/kg and 0.375 mg/kg, respectively. FIG. 5 shows similar dynamics of the group given the non-effervescent preparation of Example 1 at a G-CSF dose level of 1.5 mg/kg. FIG. 6 is a BTL dynamic curve similar to FIG. 2 curve (1.5 mg G-CSF/kg) in comparison with the control over 96 hours after administration.

Figure 1:
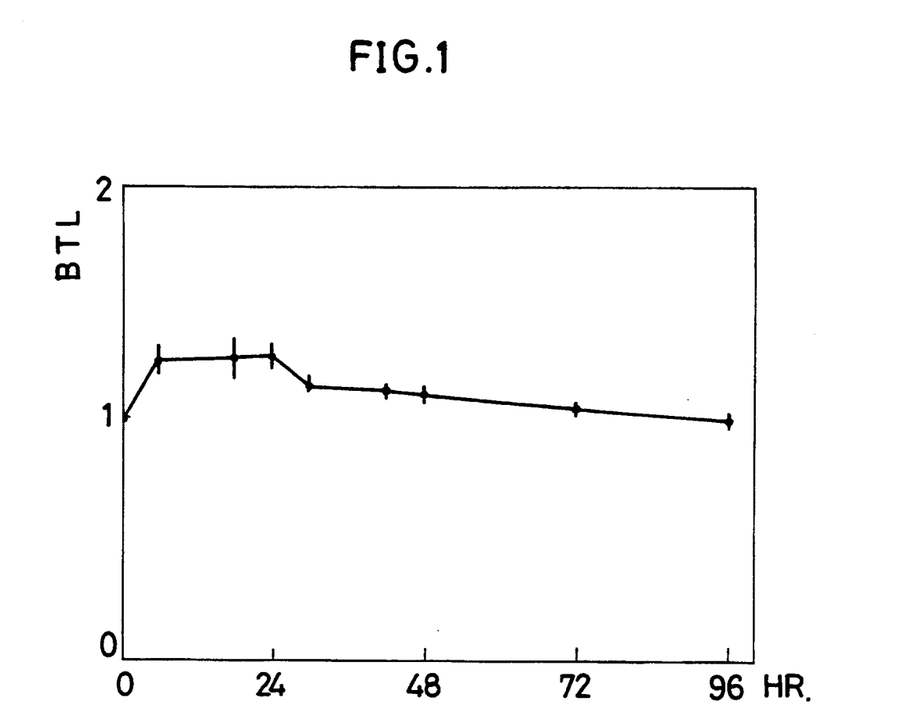
FIGS. 1, 2, 3 and 4 illustrate BTL dynamics obtained by the administration of Example 1 at a G-CSF dose level of zero (control), 1.5 Mg/Kg, 0.75 Mg/Kg respectively.
Figure 2:
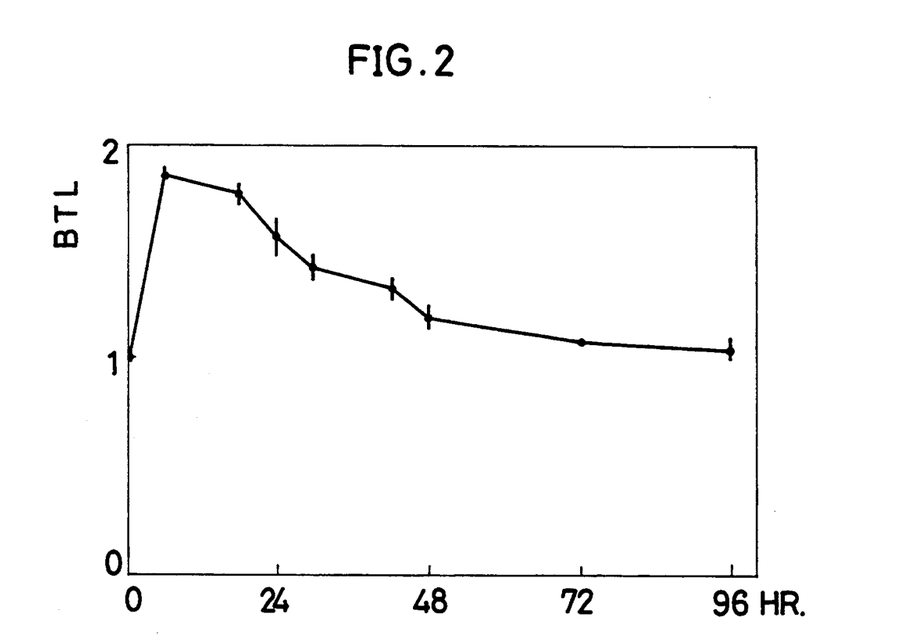
Figure 3:
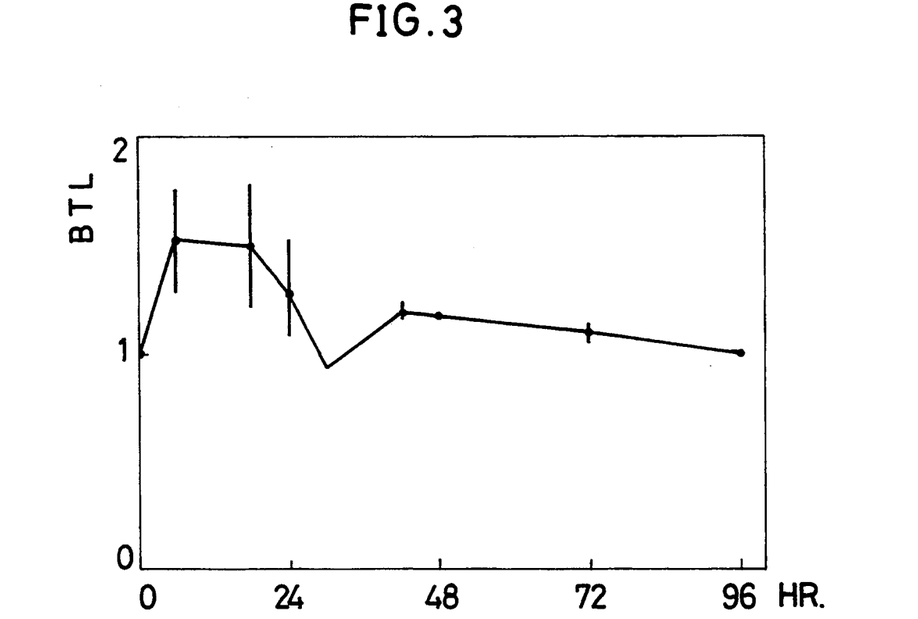
Figure 4:
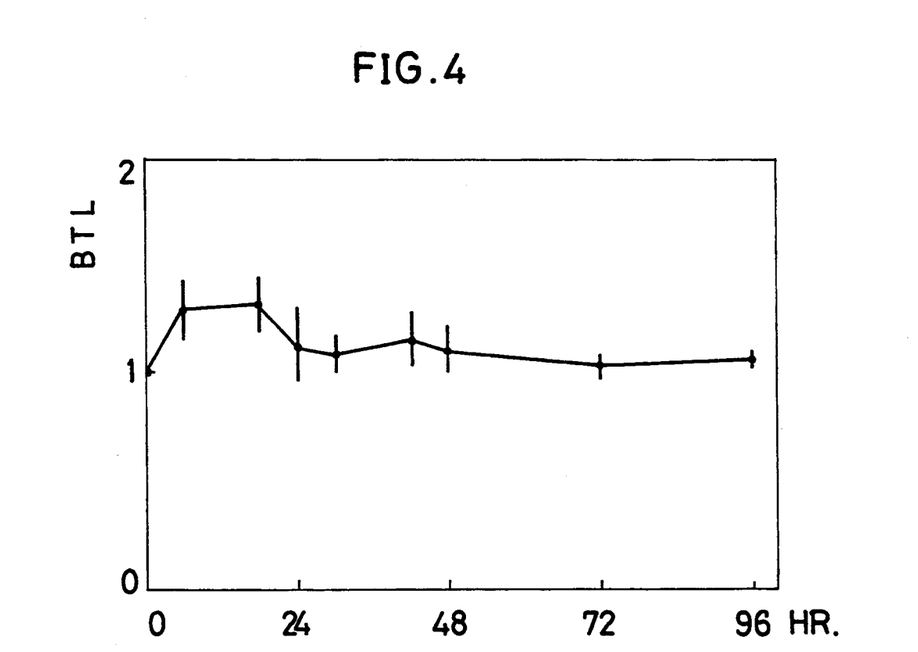

As can be seen in the drawings, a significant increase in the BTL count was observed over 48 hours at the G-CSF dose of 1.5 mg/kg compared with the control group. The BTL dynamics curves shown in FIGS. 1–4 indicate that the increase in BTL count is of a dose-dependency nature, while no significant difference may be seen in the curve of FIG. 4 (0.357 mg/kg) as compared with the control (FIG. 1). The non-effervescent preparation of Example 1 was also substantially as effective as the effervescent preparation in the increase of BTL as count as demonstrated in FIG. 5.

EXAMPLE 5

Figure 7:
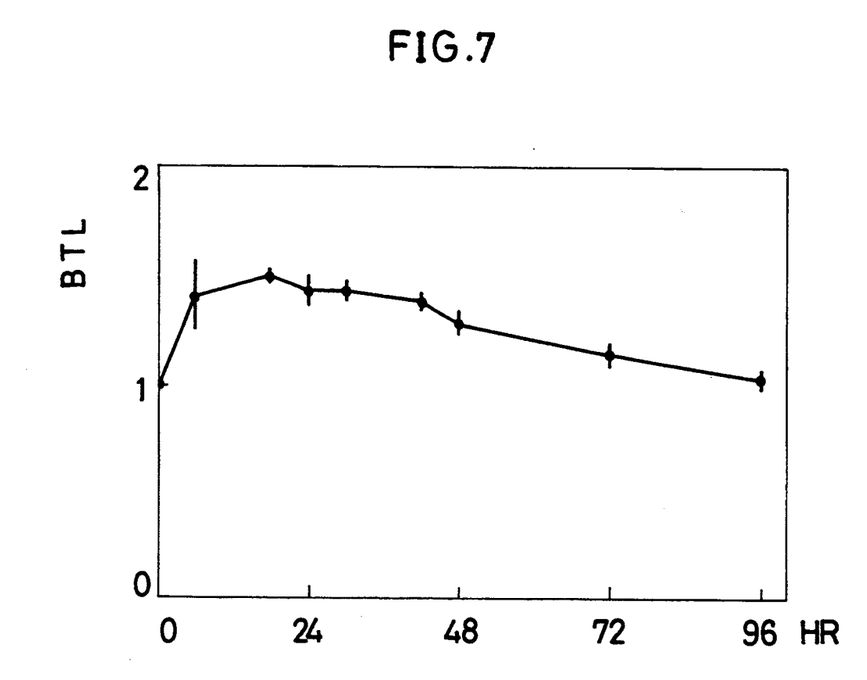
FIG. 7 is a BTL dynamics curve at a G-CSF dose level of 1.5 Mg/Kg, FIG. 8 show the dynamics of blood sugar levels expressed as the index relative to the control.

The experiments of Example 4 were repeated using the enteric preparation of Example 2 containing no L-tartaric acid. The BTL dynamics curve at a G-CSF dose level of 1.5 mg/kg is shown in FIG. 7. The increase in BTL level in FIG. 7 is not remarkable as FIG. 2, but still significant compared to the control shown in FIG. 1.

EXAMPLE 6

Figure 8:
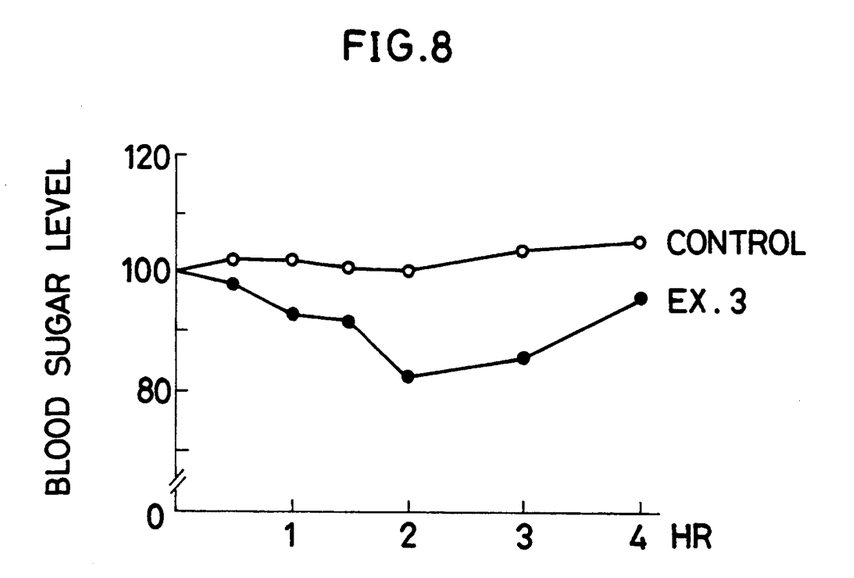

Analogous to Example 4, the enteric preparation of insulin produced in Example 3 was administered to the rat at a dose level of 2.5 mg/rat as insulin. As a control, another rat was given a placebo preparation which was free of insulin but otherwise identical to the preparation of Example 3. Blood samples were taken from the jugular vein before and after the administration of the test preparations over 4 hours. The dynamics of blood sugar levels as expressed as the index relative to the control are shown in FIG. 8. The blood sugar level decreased to nearly 80% of the control.

EXAMPLE 7

500 mg of a renin inhibitor peptide having the following formula:

M.W.=649.79, $C_{35}H_{47}N_5O_7$, 100 mg of HCO-60 and 4.2 g of L-tartaric acid were dissolved in 10 ml of methanol at 40° C. This solution was placed in a mortar, stirred with a pestle under hot air current, placed in a desiccator under vacuum to remove the solvent and pulverized with the pestle. After the addition of 200 mg of sodium bicarbonate, the mixed powder was kneaded with a small amount of methanol, extruded through a 14 mesh wire screen and dried to give granules which were then given an enteric coating of HP-55.

Analogous to Example 4, the above enteric preparation was administered to the rats at a dose level of 10 mg/rat as the renin inhibitor. As a control, another group of rats was given a drug suspended in CMC solution at the same dose level.

Blood samples were taken from the carotid artery after the administration and assayed for the concentration of the renin inhibitor using HPLC.

Figure 9:
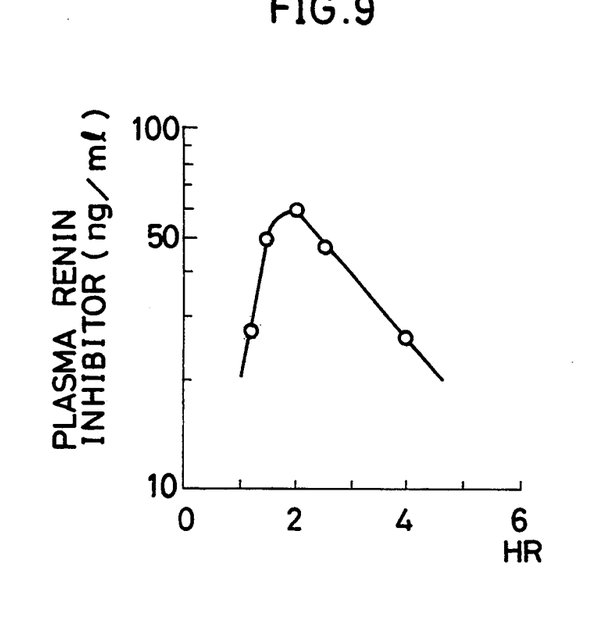
FIG. 9 is a graph showing concentration of renin inhibitor using HPLC.
Figure 10:
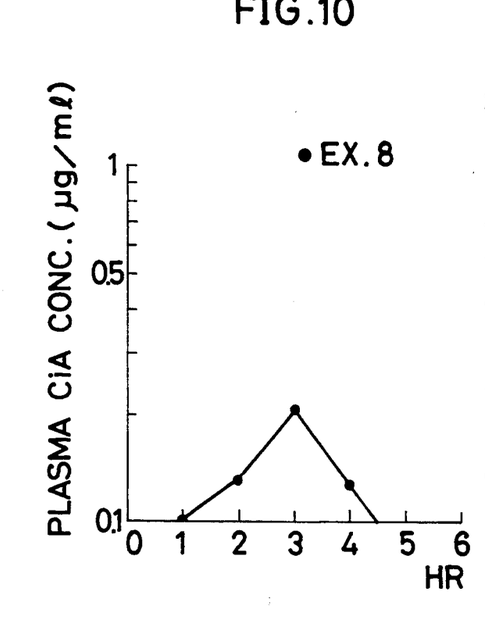
FIGS. 10, 11, 12, 13, 14, 15 are graphs showing the C;A concentrations in Male Wistar rats when using preparations from examples 10, 11, 12, 13, 14 and 15 respectively.

The concentration was less than the detection limit of 25 ng/ml for the CMC suspension whereas the concentration increased to a maximum of 60 ng/ml for the formulation of this invention as shown in FIG. 9.

EXAMPLES 8–13

100 mg of cyclosporin A (CiA) was dissolved in a mixture of 10 ml of methanol and 0.5 ml of acetone. To the solution was added an amount of HCO-60 as indicated in Table 1 below with stirring using a magnetic stirrer to make a solution. During this step, the mixture was heated to 50° C., if necessary, to promote the dissolution of HCO-60. Thereafter, an amount of various enteric materials as specified in Table 1 was dissolved in the solution in a similar manner. The resultant solution was transferred into a mortar and stirred with a pestle under hot air current at 30° C. to remove a major portion of the solvent. The resultant mass was placed in a desiccator under vacuum for 2–5 hours to completely remove the solvent and pulverized with the pestle.

TABLE 1

| Example No. | Amount of HCO-60 (mg) | Carrier material | Amount of carrier (mg) |
|---|---|---|---|
| 8 | 280 | CAP[1] | 840 |
| 9 | 140 | Eudragit[2] | 260 |
| 10 | 260 | HP-55[3] | 770 |
| 11 | 200 | " | 800 |
| 12 | 100 | " | 825 |
| 13 | 50 | " | 850 |

[1] Cellulose acetate phthalate
[2] Methacrylic acid-methyl methacrylate copolymer
[3] Hydroxypropylmethylcellulose phthalate

EXAMPLE 14

A powdered preparation produced according to any one of preceding Examples 8–13 was kneaded with a small amount of a 50:50 mixture of methanol and water. The resulting mass was extruded through a 30 mesh (500 μm) or 18 mesh (850 μm) stainless wire screen and dried under vacuum. The resulting granules were placed in a rotating drum and sprayed with a solution of Eudragit or HP-55 in acetone containing a trace amount of water. Spraying was repeated 3–6 times until a coating substantially free of pinholes was formed. Then the coated granules were dried to obtain an enteric preparation.

EXAMPLE 15

The procedure of Example 14 was followed except that the starting powder additionally contained one tenth by weight of sodium bicarbonate to give effervescent granules having an enteric coating.

EXAMPLE 16

Four male Wistar rats, weighing 400 g to 500 g, were used for each of CiA preparations produced in Examples 8–13 and for an oily solution of CiA (Sandimmun, Sadoz Ltd.) as control. CiA preparations corresponding to a CiA dose level of 7 mg/kg packed in a Teflon ® tubing (i.d., 0.4 mm, o.d., 0.6 nun) of 10 cm length were pushed into the rat duodenum through an incision on the stomach and 0.5 ml of normal saline was injected twice to flush them into the incision site.

After administration, blood samples were collected from the left carotid artery and lymph samples were collected from the thoracic lymph duct over 6 hours. The collected samples were assayed for CiA concentrations and the results are shown in FIG. 10–15.

The lymphatic availability of CiA was estimated as the percentage amount of CiA transferred into the thoracic lymphatics up to the end of the 6 hour experiment period and the results are shown in Table 2.

TABLE 2

| Preparation Ex. No. | n | Peak lymph level (μg/ml) | % of CiA transferred over 6 hours (% of dose) | Lymph flow (ml/h) |
|---|---|---|---|---|
| 8 | 1 | 41.49 | 0.67 | 0.113 |
| 9 | 2 | (32.14) | (0.78) | (0.234) |
|   |   | (44.47) | (1.53) | (0.358) |
| 10 | 1 | 8.28 | 0.14 | 0.185 |
| 11 | 3 | 74.80 ± 12.86 | 1.98 ± 0.10 | 0.273 ± 0.050 |
| 12 | 3 | 38.43 ± 1.44 | 1.13 ± 0.16 | 0.316 ± 0.030 |
| 13 | 3 | 4.86 ± 1.69 | 0.11 ± 0.05 | 0.288 ± 0.005 |
| Control | 3 | 18.86 ± 2.56 | 0.78 ± 0.11 | 0.326 ± 0.010 |

Note:
Data show the mean ± S.E. when n = 3

Figure 11:
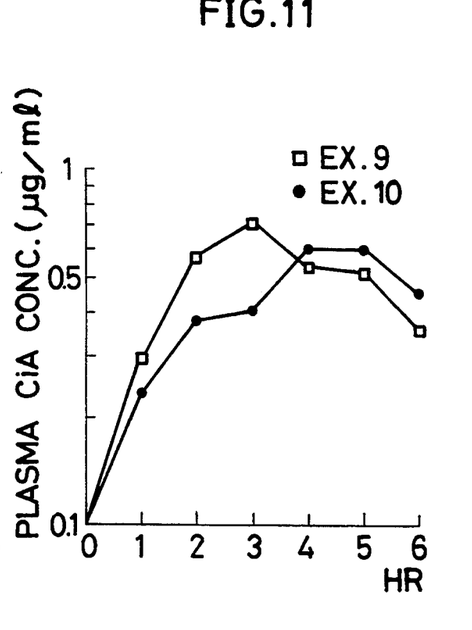
Figure 12:
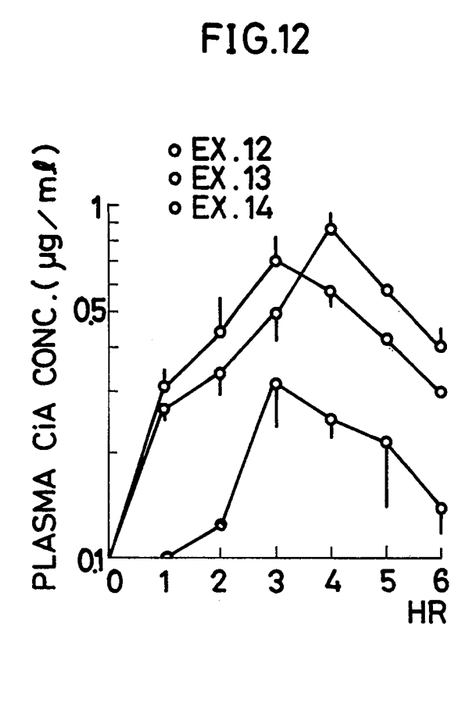
Figure 13:
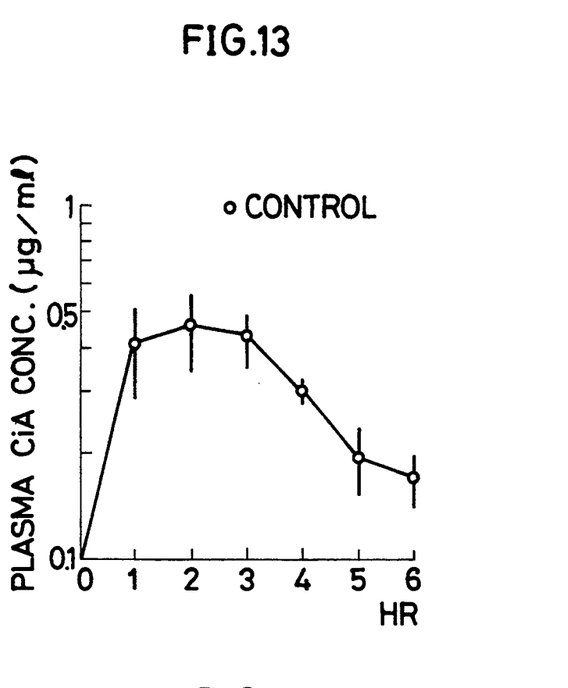
Figure 14:
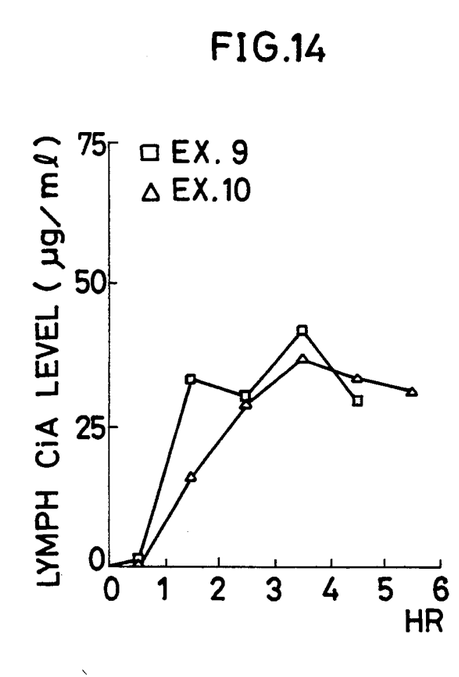
Figure 15:
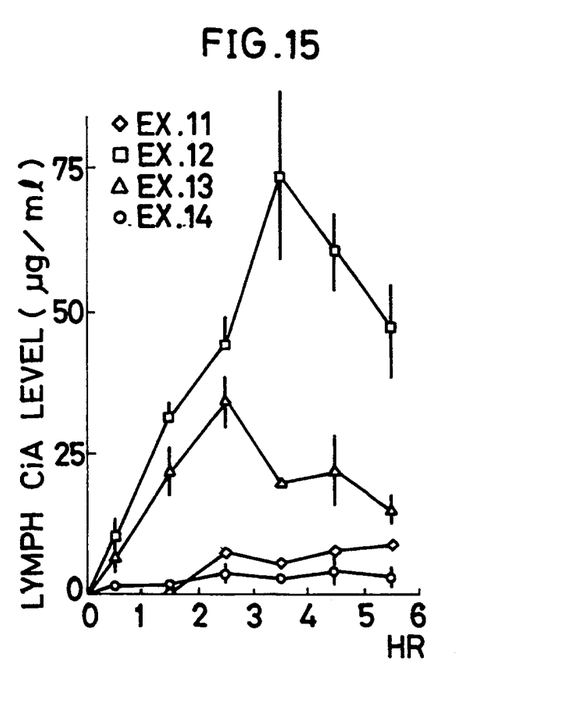

The experiments show that the CiA preparations of the present invention are comparable to the commercial oily solution in plasma CiA levels and transfer to the thoracic lymph. Some preparations exhibited higher overall transfer to the thoracic lymph than the control. Since the pharmacology of CiA is believed to be its specific inhibition of helper T-lymphocytes, this increase in transfer CiA into the thoracic lymph is considered to be great significance. As shown in FIGS. 11–13, the overall transfer of CiA in the blood stream of the CiA preparations of the present invention are also comparable or somewhat superior to the commercial oily solution.

What is claimed is:

1. A solid enteric pharmaceutical formulation consisting of a particulate intimate physical mixture of a (a) physiologically active peptide or protein, (b) a nontoxic nonionic surfactant, (c) a pharmaceutically acceptable solid organic acid selected from the group consisting of tartaric, malonic, maleic, malic, citric and cinnamic acids (d), at least 50 wt. %, based on the weight of the pharmaceutical formulation, of a pharmaceutically acceptable, enteric polymer which is soluble in a volatile organic solvent and which dissolves selectively from the mixture in duodenal juice when the mixture is ingested and, optionally, (e) either or both of a pharmaceutically acceptable solid diluent and an effervescing agent.

2. The pharmaceutical formulation of claim 1 wherein the effervescing agent is sodium bicarbonate.

3. The pharmaceutical formulation of claim 1 which contains not less than 80 wt. %, based on the weight of the formulation, of the enteric polymer.

4. The pharmaceutical formulation of claim 1, wherein the peptide or protein is insulin, human granulocyte colony-stimulating factor, a renin inhibitor peptide or cyclosporin A.

5. The pharmaceutical formulation of claim 1, wherein the organic acid is L-tartaric acid.

6. The pharmaceutical formulation of claim 1, wherein the formulation is in granule form.

7. The pharmaceutical formulation of claim 1, in tablet, capsule or other solid unit dosage form.

8. The pharmaceutical formulation according to claim 1, wherein the surfactant is selected from the group consisting of sorbitan fatty acid ester, polyoxyethylene-sorbitan fatty acid ester, polyoxyethylene-hydrogenated castor oil, fatty acid alkanolamide, sucrose fatty acid esters, glycerol mono-, di- and trioctanoate, and the enteric material is selected from the group consisting of cellulose acetate phthalate, hydroxypropylmethylcellulose succinate, hydroxypropylmethylcellulose phthalate, carboxylmethylethylcellulose and methacrylic acid-methyl methacrylate copolymer.

9. The enteric pharmaceutical formulation according to claim 1, in the form of a particulate mixture of the physiologically active peptide or protein and the surfactant, with an enteric coating on the particles of the mixture of the enteric material.

10. The enteric pharmaceutical formulation according to claim 9, wherein the surfactant is selected from the group consisting of sorbitan fatty acid ester, polyoxyethylenesorbitan fatty acid ester, polyoxyethylene-hydrogenated castor oil, fatty acid alkanolamide, sucrose fatty acid esters, glycerol mono-, di- and trioctanoate, and the enteric material is selected from the group consisting of cellulose acetate phthalate, hydroxy propylmethylcellulose succinate, hydroxypropylmethylcellulose phthalate, carboxylmethylethylcellulose and methacrylic acid-methyl methacrylate copolymer.

11. An enteric pharmaceutical formulation according to claim 10, wherein the physiologically active peptide or protein is selected from the group consisting of angiotensin II antagonist peptide, bradykinin, calcitonin-gene associated factor, tissue plasminogen activators, cholecystokinin, delta sleep-inducing peptide (DSIP), β-endorphin, atriopeptin, α-and β-melanocyte-stimulating hormone, nerve peptide, nerve growth factor (NGF), gastrin antagonist peptide, neurotensin, somatostatin, the colony-stimulating factors G-CSF and GM-CSF, interferon, thymopoietin, tumor necrosis factor, growth hormone, growth hormone-carrier protein complex, human atrial natriuretic peptide (HANP), insulin, luteinizing hormone-releasing factor (LHRH), streptokinase, erythropoietin, urokinase, lysozyme, vasopressin (8- lysine and 8-arginine), oxytocin, desmopressin, cytochrome C, histamine-releasing factor, platelet related growth factor, human chorionic gonadotropin (HCG), human growth hormone (HGH), adrenocorticotropin (ACTH), calcitonin, parathyroid hormone, Factor XIII, Factor IX, MSH release inhibiting factor, enkephalin, thyrotropin releasing hormone, interleukins and renin inhibitor peptides.

12. The pharmaceutical formulation according to claim 11, wherein the surfactant is selected from the group consisting of: sorbitan fatty acid ester, polyoxyethylene-sorbitan fatty acid ester, polyoxyethylene-hydrogenated castor oil, fatty acid alkanolamide, sucrose fatty acid esters, glycerol mono-, di- and trioctanoate, and the enteric material is selected from the group consisting of cellulose acetate phthalate, hydroxypropylmethylcellulose succinate, hydroxypropylmethylcellulose phthalate, carboxylmethylethylcellulose and methacrylic acid-methyl methacrylate copolymer.

13. The pharmaceutical formulation of claim 11, wherein the peptide or protein is insulin, human granulocyte colony-stimulating factor, a renin inhibitor peptide or cyclosporin A.

14. A solid ingestible enteric pharmaceutical formulation consisting of a solid particulate mixture of (a) a physiologically active peptide or protein, (b) a nontoxic nonionic surfactant, (c) a pharmaceutically acceptable solid organic acid selected from the group consisting of tartaric, malonic, maleic, malic, citric and cinnamic acids and, optionally, (d) an inert solid diluent; the particles of which are covered with at least 50 wt. %, based on the weight of the formulation, of a polymer as a discrete enteric coating which covers the surface of the individual particles of the mixture, which coating is soluble in a volatile organic solvent and dissolves selectively in duodenal juice when the mixture is ingested.

15. The pharmaceutical formulation of claim 14, wherein the effervescing agent is sodium bicarbonate.

16. The pharmaceutical formulation of claim 14, which contains not less than 80 wt. %, based on the weight of the formulation, of the enteric polymer.

17. The pharmaceutical formulation of claim 14, wherein the peptide or protein is insulin, human granulocyte colony-stimulating factor, a renin inhibitor peptide or cyclosporin A.

18. The pharmaceutical formulation of claim 14, wherein the organic acid is L-tartaric acid.

19. The pharmaceutical formulation of claim 14, wherein the formulation is in granule form.

20. The pharmaceutical formulation of claim 14, in tablet, capsule or other solid unit dosage form.

* * * * *